(12) United States Patent
Kim et al.

(10) Patent No.: US 6,451,595 B1
(45) Date of Patent: Sep. 17, 2002

(54) HIGH EFFICIENCY RETROVIRAL VECTORS THAT CONTAIN NONE OF VIRAL CODING SEQUENCES

(75) Inventors: Sunyoung Kim; Seung Shin Yu; Jong-mook Kim, all of Seoul (KR)

(73) Assignee: Viromed Limited, Seoul (KR)

( * ) Notice: Subject to any disclaimer, the term of this patent is extended or adjusted under 35 U.S.C. 154(b) by 0 days.

(21) Appl. No.: 09/463,067

(22) PCT Filed: Jul. 24, 1999

(86) PCT No.: PCT/KR99/00334

§ 371 (c)(1), (2), (4) Date: Jan. 14, 2000

(87) PCT Pub. No.: WO00/00629

PCT Pub. Date: Jan. 6, 2000

(30) Foreign Application Priority Data

Jun. 26, 1998 (KR) ............................................. 98-24478
Jun. 22, 1999 (KR) ............................................. 99-23398

(51) Int. Cl.[7] ...................... C12N 15/867; C12N 15/09; C12N 1/20; C12N 7/01; C07H 21/04
(52) U.S. Cl. ............................. 435/320.1; 435/235.1; 435/69.1; 435/325; 435/243; 435/252.3; 435/252.33; 435/456; 536/23.1; 536/23.4; 536/24.1
(58) Field of Search .................... 435/320.1, 252.3, 435/252.33, 243, 471, 69.1, 235.1, 456, 325; 536/23.1, 23.4, 24.1

(56) References Cited

U.S. PATENT DOCUMENTS 5,688,688 A 11/1997 Luciw et al.
5,858,744 A * 1/1999 Baum et al. ............. 435/172.3

FOREIGN PATENT DOCUMENTS

| WO | 9424298 | 10/1994 |
|----|---------|---------|
| WO | 9522617 | 8/1995 |
| WO | 9812338 | 3/1998 |

* cited by examiner

*Primary Examiner*—David Guzo
*Assistant Examiner*—Gerald G. Leffers, Jr.
(74) *Attorney, Agent, or Firm*—Bachman & LaPointe, P.C.

(57) ABSTRACT

The present invention relates to improved retroviral vectors for gene therapy. In this invention, retroviral vectors with higher safety and efficiency are constructed from MLV-based starting vectors, MON and MIN. The improved vectors have the following features: 1) sequences corresponding to MLV-derived pol gene are completely deleted in the vectors, avoiding homologous recombination which has been a baffling problem in conventional retroviral vectors, 2) a heterologous intron, splicing acceptor and/or non-coding sequence are/is inserted into the upstream position of a cloning site, maximizing the expression of a foreign gene through efficient splicing, 3) the vectors contain either the full-length U3 sequence of 5' LTR or a strong heterologous promoter instead, permitting the abundant production of RNA, 4) either IRES (Internal Ribosomal Entry Site) or internal SV40 minimal promoter is inserted into the downstream position of cloning site, enabling the simultaneous expression of two or more foreign genes. Since the improved retroviral vectors of this invention turn out to be safe and to express the foreign gene efficiently, they are useful for gene therapy and the like.

19 Claims, 13 Drawing Sheets

MIN-AI    Human β-actin gene    (+717 to +849)

MIN-GI    Human GAPDH gene    (+185 to +317)

MIN-EI    Human EF1-α gene    (+772 to +1008)

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: HHIR primer

<400> SEQUENCE: 1
aagcttatct gaaagacccc                                                        20

<210> SEQ ID NO 2
<211> LENGTH: 22
<212> TYPE: DNA
<213> ORGANISM: Artificial Sequence
<220> FEATURE:
<223> OTHER INFORMATION: R523Bam primer

<400> SEQUENCE: 2
ggatcccaaa aattcagacg ga                                                     22

<210> SEQ ID NO 3
<211> LENGTH: 20
<212> TYPE: DNA
<213> ORGANISM: Artificial Sequence
<220> FEATURE:
<223> OTHER INFORMATION: CATATGN primer

<400> SEQUENCE: 3
ccatggagaa aaaaatcact                                                        20

<210> SEQ ID NO 4
<211> LENGTH: 24
<212> TYPE: DNA
<213> ORGANISM: Artificial Sequence
<220> FEATURE:
<223> OTHER INFORMATION: CATSTOP primer

<400> SEQUENCE: 4
ggatccttac gccccgccct gcca                                                   24

<210> SEQ ID NO 5
<211> LENGTH: 39
<212> TYPE: DNA
<213> ORGANISM: Artificial Sequence
<220> FEATURE:
<223> OTHER INFORMATION: SV40-5 primer

<400> SEQUENCE: 5
cggatccgtc gacgttaact catgcatctc aattagtca                                   39

<210> SEQ ID NO 6
<211> LENGTH: 18
<212> TYPE: DNA
<213> ORGANISM: Artificial Sequence
<220> FEATURE:
<223> OTHER INFORMATION: Neo-3 primer

<400> SEQUENCE: 6
ctcgagtcag aagaactc                                                          18

<210> SEQ ID NO 7
<211> LENGTH: 28
<212> TYPE: DNA
<213> ORGANISM: Artificial Sequence
<220> FEATURE:
<223> OTHER INFORMATION: RI5 primer

<400> SEQUENCE: 7
gggaattctc agatcgcctg gagacgcc                                               28

<210> SEQ ID NO 8
<211> LENGTH: 21
<212> TYPE: DNA
<213> ORGANISM: Artificial Sequence

```
<220> FEATURE:
<223> OTHER INFORMATION: CMVexon2.3 primer

<400> SEQUENCE: 8
aagcttcgtg tcaaggacgg t                                       21

<210> SEQ ID NO 9
<211> LENGTH: 15
<212> TYPE: DNA
<213> ORGANISM: Artificial Sequence
<220> FEATURE:
<223> OTHER INFORMATION: SA Top oligomer

<400> SEQUENCE: 9
gatctctcca cagga                                              15

<210> SEQ ID NO 10
<211> LENGTH: 15
<212> TYPE: DNA
<213> ORGANISM: Artificial Sequence
<220> FEATURE:
<223> OTHER INFORMATION: SA bottom oligomer

<400> SEQUENCE: 10
agaggtgtcc tctag                                              15

<210> SEQ ID NO 11
<211> LENGTH: 26
<212> TYPE: DNA
<213> ORGANISM: Artificial Sequence
<220> FEATURE:
<223> OTHER INFORMATION: exon 13 primer

<400> SEQUENCE: 11
cgggatccgt cactcttggc acgggg                                  26

<210> SEQ ID NO 12
<211> LENGTH: 40
<212> TYPE: DNA
<213> ORGANISM: Artificial Sequence
<220> FEATURE:
<223> OTHER INFORMATION: 3LTR5 primer

<400> SEQUENCE: 12
ggatcctcga ggataaaata aaagatttta tttagtctcc                   40

<210> SEQ ID NO 13
<211> LENGTH: 26
<212> TYPE: DNA
<213> ORGANISM: Artificial Sequence
<220> FEATURE:
<223> OTHER INFORMATION: 3LTR3 primer

<400> SEQUENCE: 13
gaattcaatg aaagaccccc gctgac                                  26

<210> SEQ ID NO 14
<211> LENGTH: 50
<212> TYPE: DNA
<213> ORGANISM: Artificial Sequence
<220> FEATURE:
<223> OTHER INFORMATION: 5LTR3 primer

<400> SEQUENCE: 14
ggatccgcgg gcccacgcgt attttcagac aaatacagaa acacagtcag        50
```

<210> SEQ ID NO 15
<211> LENGTH: 36
<212> TYPE: DNA
<213> ORGANISM: Artificial Sequence
<220> FEATURE:
<223> OTHER INFORMATION: beta-actin 5 primer

<400> SEQUENCE: 15
acgcgtgccc agcaccccaa ggcggccaac gccaaa          36

<210> SEQ ID NO 16
<211> LENGTH: 37
<212> TYPE: DNA
<213> ORGANISM: Artificial Sequence
<220> FEATURE:
<223> OTHER INFORMATION: beta-actin 3 primer

<400> SEQUENCE: 16
gctagcggtg agctgcgaga atagccgggc gcgctgt         37

<210> SEQ ID NO 17
<211> LENGTH: 36
<212> TYPE: DNA
<213> ORGANISM: Artificial Sequence
<220> FEATURE:
<223> OTHER INFORMATION: EF1 alpha 5 primer

<400> SEQUENCE: 17
acgcgtggca attgaaccgg tgcctagaga aggtgg          36

<210> SEQ ID NO 18
<211> LENGTH: 36
<212> TYPE: DNA
<213> ORGANISM: Artificial Sequence
<220> FEATURE:
<223> OTHER INFORMATION: EF1 alpha 3 primer

<400> SEQUENCE: 18
gctagctttg gcttttaggg gtagttttca cgacac          36

<210> SEQ ID NO 19
<211> LENGTH: 41
<212> TYPE: DNA
<213> ORGANISM: Artificial Sequence
<220> FEATURE:
<223> OTHER INFORMATION: Gint5 primer

<400> SEQUENCE: 19
acgcgtatcg atagatctgt cgacgtgatg cggcgcgggc t    41

<210> SEQ ID NO 20
<211> LENGTH: 39
<212> TYPE: DNA
<213> ORGANISM: Artificial Sequence
<220> FEATURE:
<223> OTHER INFORMATION: Gint3 primer

<400> SEQUENCE: 20
gcggccgcgt taacggatcc atggtgtctg agcgatgtg       39

HIGH EFFICIENCY RETROVIRAL VECTORS THAT CONTAIN NONE OF VIRAL CODING SEQUENCES

FIELD OF THE INVENTION

The present invention relates to improved retroviral vectors for gene therapy. Particularly, this invention relates to safe and efficient retroviral expression vectors, where all of the retroviral genes, i.e. gag, env and pol, are deleted completely; where a heterologous intron, splicing acceptor, and/or non-coding sequence are/is inserted into the upstream position of cloning site for a foreign gene; where a heterologous internal promoter or an internal ribosomal entry site (hereinafter, referred to as "IRES") is inserted into the downstream position of the cloning site; and where the full-length U3 sequence of 5' LTR (Long Terminal Repeat) or a strong heterologous promoter controls the expression of the foreign gene.

BACKGROUND

Retroviral vectors have been used for gene therapy more frequently than any other vector, being employed in more than 50% of the approved clinical protocols worldwide (Wiley—Journal of Gene Medicine Website. Although Murine Leukemia Virus (hereinafter, referred to as "MLV")-based vectors are used dominantly, there are still many problems with the retroviral vectors in clinical use. The most serious problem is their safety; retroviral vector is one of the viral vector and thus may be converted in cells into replication-competent retrovirus (hereinafter, referred to as "RCR") Above all, RCR production through homologous recombination has been a matter of grave concern.

All available retroviral vectors contain significantly long viral coding sequences. Since these sequences are also present in the genome of packaging cells from which the packaged vectors are released, it has bees suggested that homologous recombination may occur between the same nucleotide sequence in the packaging genome and the vector, resulting in the production of RCR, which was reported by Miller et al. (Miller et al., Human Gene Ther., 1: 5, 1990).

Two types of MLV-based retroviral vectors, LN series vectors and MFG vector, have been most frequently used for gene therapy (Miller and Roseman, Biotechniques, 7:980–990, 1989; Dranoff et al., Proc. Nat'l. Acad. Sci. USA 90: 3539–3543, 1993). While the expression of a foreign gene in LN series vectors is controlled by a heterologous internal promoter or by LTR, transcription level in MFG vector is under the control of LTR, and the foreign gene is expressed as a form of either genomic RNA or spliced subgenomic RNA. The LN series vectors, that are often considered the first generation retroviral vectors, contain the 420-bp gag coding sequence. Although this region has been thought to play an important role in viral packaging, it has been disclosed that gag region can be deleted without any significant effect on the viral packaging and titer under some conditions (Kim et al., J. Virol., 71: 994–1004, 1998).

Compared with LN series vectors, MFG vector is known to drive more stable and higher levels of gene expression, and produce higher viral titers in most of human- or mouse-derived cell lines (Byun et al., Gene Ther., 3: 780–788, 1996). However, MFG vector contains even more viral coding sequences, 420-bp for gag, 377-bp for pol, and 99-bp for env, raising the possibility of even higher frequency of producing RCR than the LN series vectors.

To overcome these disadvantages associated with conventional retroviral vectors, we, the inventors of this invention, constructed a retroviral vector (KOREA PATENT APPLICATION NO: 97-48095), which had several features as follows:

- transcripts of the cloned gene was effectively spliced, producing higher expression levels of the gene,
- gag and env sequences were completely deleted without a loss of viral titer,
- IRES was used for the simultaneous expression of two or more genes in a vector,
- multicloning site was inserted into the vector to facilitate the cloning of foreign gene Since gag and env sequences were deleted from the retroviral vectors, the safety of the vectors was increased when compared with those of other retroviral vectors. However, this vector still contains the 377-bp pol coding sequence that harbors the splicing acceptor sequence as well as its downstream sequence containing the 284-bp leader (transcribed but untranslated) sequence for env, because the deletion of pol sequence would lead to abnormal or inefficient splicing. Since the 377-bp for pol sequence is also present in the genome of packaging lines, the possibility of homologous recombination resulting in RCR production still remains in the vector.

To develop novel retroviral vectors with elevated efficiency of gene expression as well as enhanced safety, we have constructed the retroviral vectors that do not contain ;any viral coding sequence. This invention is performed by constructing retroviral vectors, where MLV-derived pol gene is completely deleted, excluding the possibility of RCR production through homologous recombination in packaging cell line; where a heterologous intron, splicing acceptor, and/or non-coding sequence are/is inserted into the upstream position of cloning site for a foreign gene, maximizing the efficiency of gene expression; where either 5' LTR or human cytomegalovirus (hereinafter, referred to as "HCMV") major immediate early promoter (MIEP: the promoter of ie1 gene) is employed as cis-element for the regulation of foreign gene expression; and where either a heterologous internal promoter or an IRES is inserted in the the downstream position of the cloning site, allowing the simultaneous expression of two or more foreign genes.

SUMMARY OF THE INVENTION

It is an object of this invention to provide safe retroviral vectors where foreign gene(s) is/are expressed in higher levels and thus can be efficiently used for gene therapy.

In accordance with the present invention, the foregoing object is readily obtained.

This invention provides MLV-based retroviral vectors wherein the MLV-coding gag, env and pol sequences are completely deleted.

In one aspect, the MLV-based retroviral vectors of this invention may contain a heterologous intron and/or a heterologous splicing acceptor which are/is inserted into the upstream position of cloning site for a foreign gene.

In another aspect, the MLV-based retroviral vectors of this invention may contain a heterologous non-coding sequence inserted into the upstream position of cloning site for a foreign gene.

In further aspect, the full-length U3 sequence (−419 to −1 bp) of MLV 5' LTR may be replaced with a heterologous promoter in the MLV-based retroviral vectors of this invention.

In still further aspect, the MLV-based retroviral vectors of this invention may contain a heterologous promoter in the downstream position of cloning site for a foreign gene.

This invention also provides the E. coli strains transformed with the MLV-based retroviral vectors of this invention.

Further features of the present invention will appear hereinafter.

DETAILED DESCRIPTION OF PREFERRED EMBODIMENTS

The present invention provides both safe and efficient retroviral vectors that are derived from MLV-based vectors, specifically from MON or MIN. In the vectors of this invention, retroviral genes (gag, env and pol coding sequences) are completely deleted; a heterologous intron, splicing acceptor, and/or non-coding sequence are/is inserted into the upstream position of cloning site for a foreign gene; a strong heterologous promoter is contained in 5' LTR; and a heterologous promoter or an IRES is positioned in the downstream position of the cloning site.

Particularly, in the vectors of this invention, since pol coding sequence containing a splicing acceptor is completely deleted, the possibility of homologous recombination, which has been a disadvantage of the conventional retroviral vectors, can be excluded.

Deleting pol sequence leads to the reduction of gene expression level. To restore the reduced expression efficiency and virus titer, various retroviral vectors are provided in this invention, as follows:

This invention provides retroviral vectors where a heterologous intron and/or splicing acceptor are/is inserted into the upstream position of cloning site for a foreign gene in order to complement the deleted splicing acceptor that overlaps with the 3' portion of pol coding sequence. All the introns and/or splicing acceptors of known viral or cellular genes may be used for this purpose, preferably the introns and/or splicing acceptors of HCMV ie1 (UL123) gene, elongation factor 1α (hereinafter, referred to as "EF1α") gene, glyceraldehyde 3-phosphate dehydrogenase (hereinafter, referred to as "GAPDH") gene, β-actin gene etc.

This invention also provides retroviral vectors where a heterologous non-coding sequence is inserted in the upstream position of the cloning site. The non-coding sequence is used to promote translational efficiency, and defined as a transcribed DNA sequence that is not translated to a protein, including intron and untranslated exon. Preferably, the non-coding sequence is selected from the group comprising the non-coding sequences of HCMV ie1 (UL123) gene, EF1α gene, GAPDH gene, and β-actin gene. The insertion of heterologous non-coding sequence enables both the efficient splicing of foreign gene transcript and the effective translation of subgenomic RNA.

In addition, this invention provides retroviral vectors where a heterologous internal promoter or IRES is harbored In the downstream position of the cloning site.

Finally, this invention provides retroviral vectors where either a full-length U3 sequence of 5' LTR or a strong heterologous promoter is contained.

Hereinafter, the present invention is described in detail.

1. The Deletion of Pol Coding Sequence: ΔSA Construction

Figure 1:
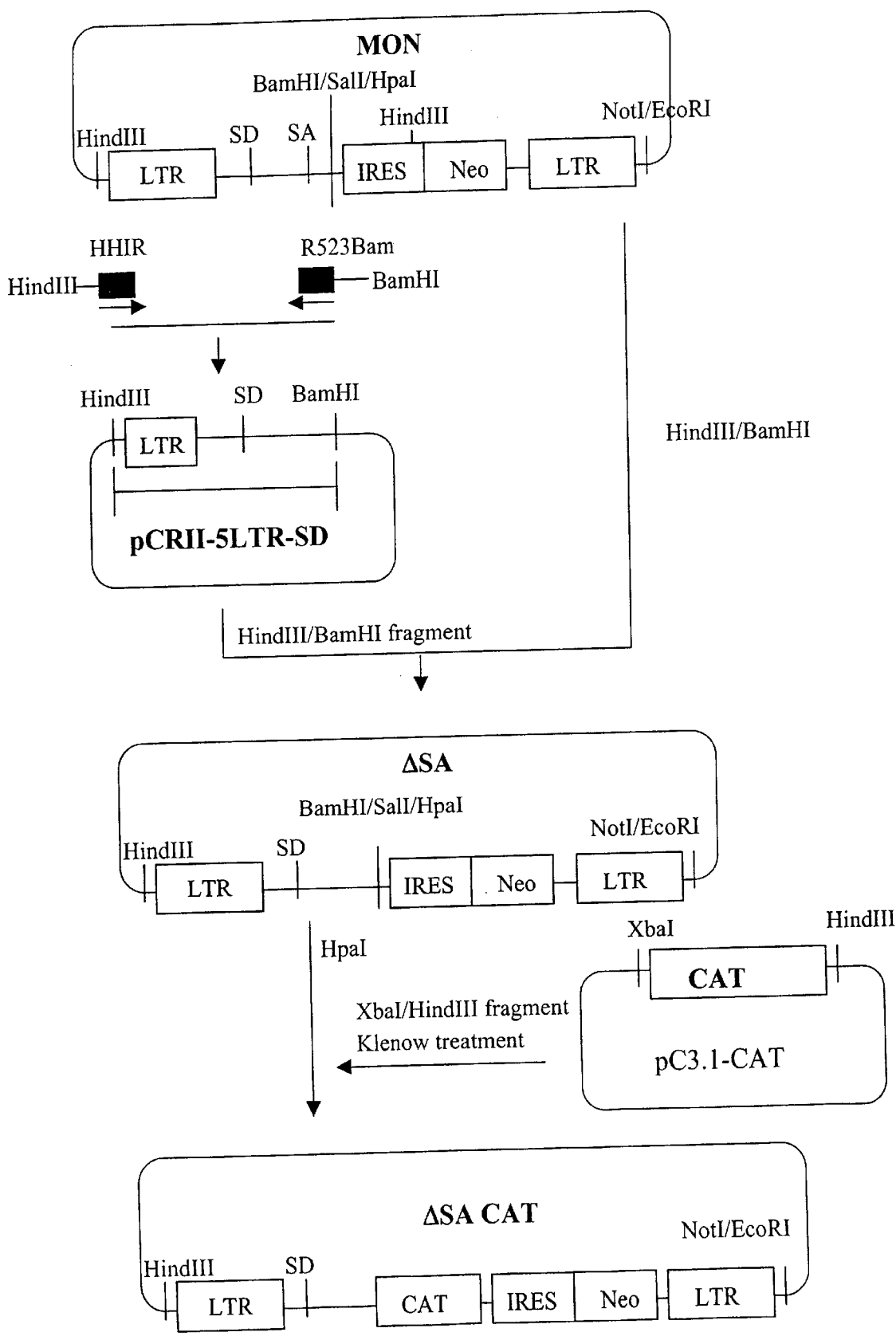
FIG. 1 represents the procedure where pol-coding region is deleted from MON vector to construct (ΔSA vector, and then the CAT gene is inserted into the (ΔSA vector to produce (ΔSA-CAT vector, FIG. 2 schematically represents the structures of retroviral vectors containing the intron and/or exon of HCMV ie1 (UL123) gene, FIG. 3a represents the procedure where a SV40 minimal promoter-neo cassette is substituted for an IRES-neo cassette to obtain MSN vector, and then SN-3LTR vector is constructed through the insertion of the fragment containing SV40 minimal promoter and MLV 3' LTR into pUC18, FIG. 3b represents the procedure where a chimeric LTR containing HCMV major immediate early promoter is inserted into the SN-3LTR vector, FIG. 4a represents the procedure where a DNA fragment containing the exon 1, intron A and partial exon 2 of HCMV ie1 (UL123) gene is inserted into pCM vector to construct DON1.2 vector, and then the bacterial CAT gene is inserted into the DON1.2 to produce DON1.2-CAT, FIG. 4b represents the procedure where a DNA fragment containing the partial intron A and partial exon 2 of HCMV ie1 (UL123) gene is inserted into pCM vector to construct DON2 vector, and then the bacterial CAT gene is inserted into the DON2 to produce DON2-CAT, FIG. 4c represents the procedure where a splicing acceptor of mouse immunoglobulin gene and the exon 1 of HCMV ie1 (UL123) gene are inserted into pCM vector to construct DONSA1 vector, and then the bacterial CAT gene is inserted into the DONSA1 to produce DONSA1-CAT, FIG. 5 schematically represents the structures of retroviral vectors containing the introns and exons of human genes, FIG. 6 represents the procedure where a DNA fragment containing MLV 5' and 3' LTR is prepared and inserted into pUC18 to give p53LTR vector, and then MIN vector is constructed through the insertion of the IRES-neo cassette isolated from pCBIN into the p53LTR.

To develop retroviral vectors with improved safety, that is, retroviral vectors without the homologous recombination activity, pol coding sequence including a splicing acceptor was deleted from MON vector (KOREA PATENT APPLICATION NO: 97-48095), constructing a deletion mutant vector, ΔSA. In addition, ΔSA-CAT vector was constructed through the insertion of a bacterial CAT (; chloramphenicol acetyltransferase) as a reporter gene (see FIG. 1). Subsequently, the cell lines transfected or transduced with the ΔSA-CAT were prepared and brought to CAT assay. The CAT assay disclosed that the viral titer of the deletion mutant was comparable to that of parental vector MON-CAT but the gene expression was reduced (see Table 1). These results proposed that pol gene containing splicing acceptor be involved in the regulation of a foreign gene expression in a vector.

As expected from the results, the expression level of a foreign gene will be elevated if a heterologous splicing acceptor and/or intron are/is inserted into the upstream position of cloning site for a foreign gene so as to complement the splicing site deleted concommitantly with the pol gene. However, if the splicing takes place too much, the ratio of subgenomic RNA to genomic RNA will increase, leading to the decrease of viral titers in spite of the high levels of gene expression.

To construct the ideal retroviral vectors, therefore, the vectors should be designed so that the rates of transcription, splicing and translation may be balanced in transfected or transduced cell line. In other words, preferable are the vectors where a foreign gene is transcribed abundantly and the amount of genomic RNA is balanced with the amount of subgenomic RNA, so that genomic RNA may be produced enough to be packaged into viral particles and that subgenomic RNA may be translated into the plenty of protein encoded by the foreign gene. In this invention, retroviral vectors are provided, where various non-coding sequences originated from viral or cellular genes are inserted into the deletion mutant vector, and then it is investigated whether this insertion has an effect on the viral titers and gene expression levels.

2. The Insertion of a Heterologous DNA Sequence Enhancing Splicing and Translational Efficiency: DON1.2. DON2 and DONSA1 Construction In order to keep the balance of splicing rate and gene expression rate as well as to elevate the overall yield of viral RNA, retroviral vectors were constructed where the U3 region of MLV 5' LTR was replaced with a strong promoter, HCMV major immediate early promoter, and where a heterologous non-coding sequence was inserted.

Figure 2:
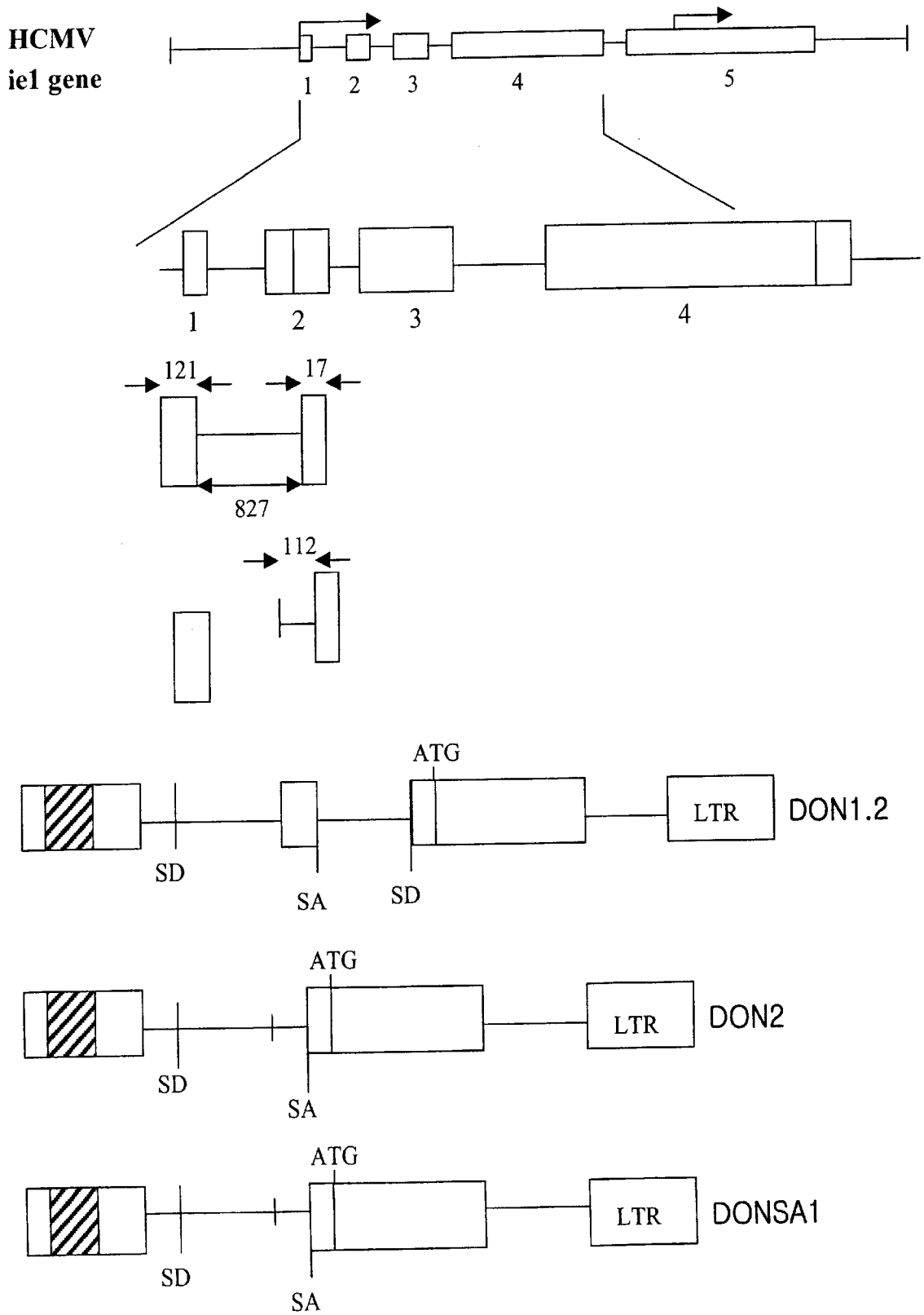
Figure 3A:
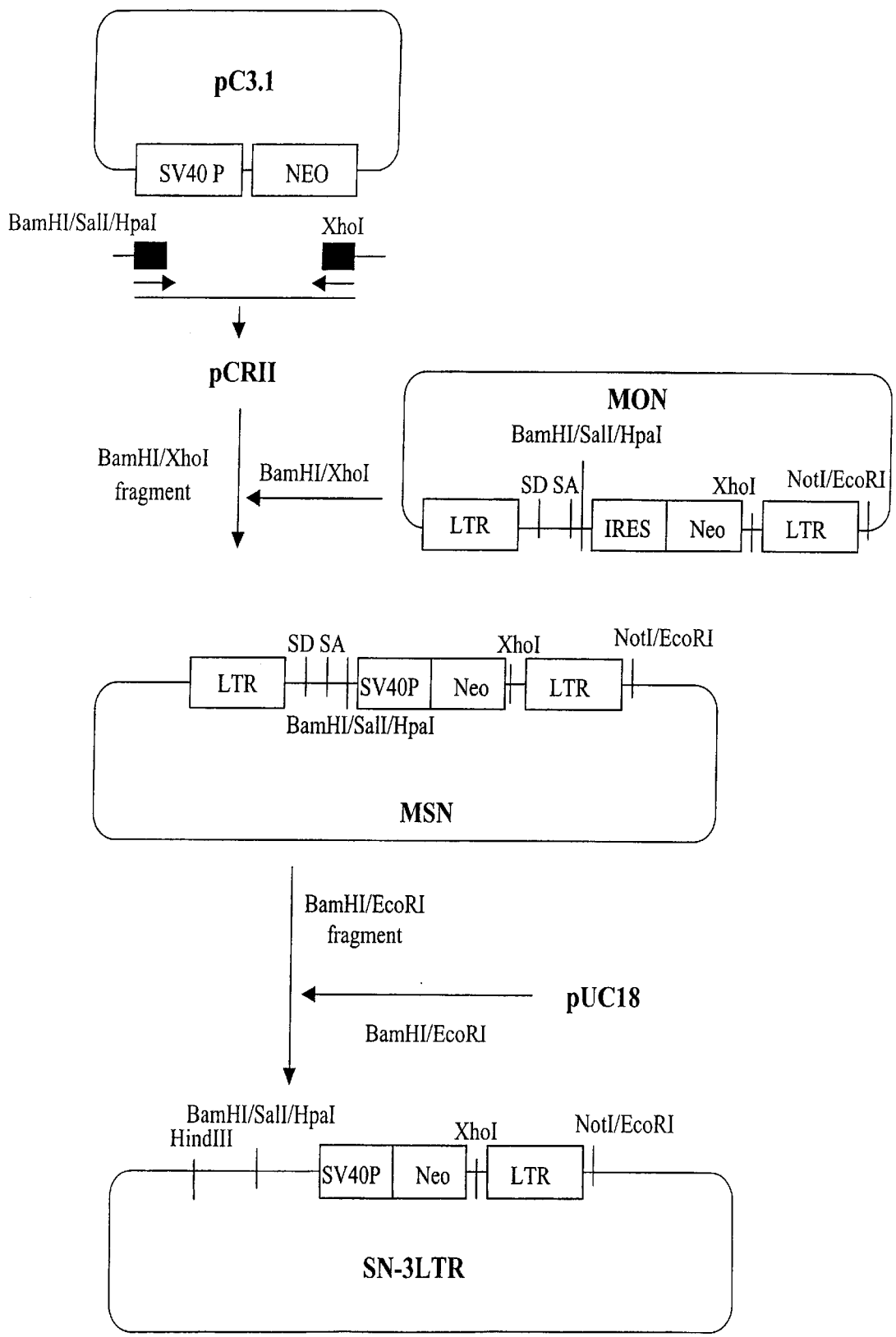
Figure 3B:
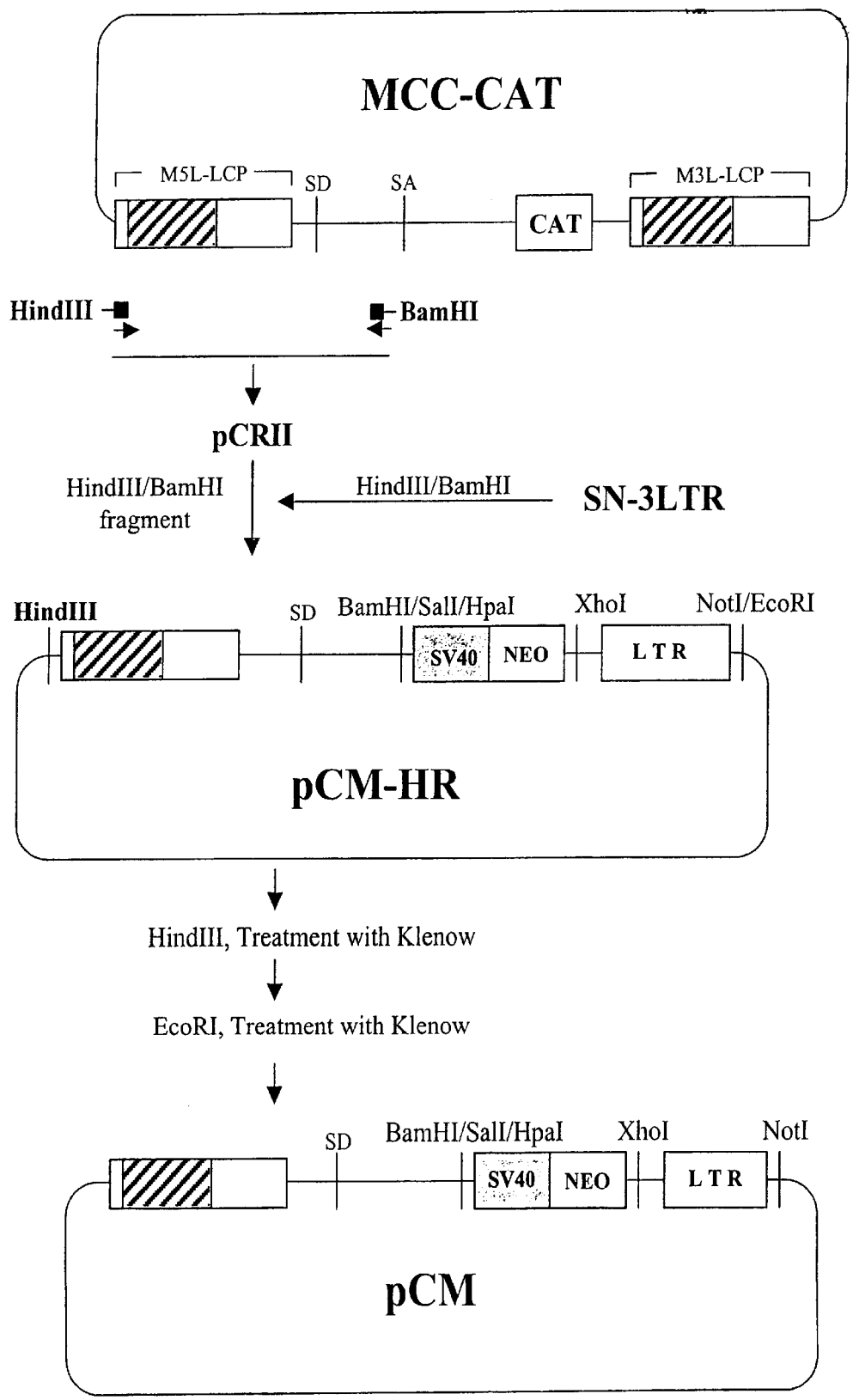

In a preferred embodiment, the untranslated exon and/or intron of HCMV ie1 (UL123) gene were/was employed as the heterologous non-coding sequence which was inserted into the upstream position of the cloning site of the vector (see FIG. 2). It has been known that the exon and/or intron sequences of HCMV ie1 (UL123) gene enhance the translation efficiency when inserted into an expression vector.

Particularly, pCM vector was prepared as follows: all of retroviral coding sequences were deleted; the full-length U3 sequence of 5' LTR was replaced with HCMV major immediate early promoter, with the MLV-derived 3'LTR kept up; and SV40 promoter-neo cassette was employed as a heterologous internal promoter. Subsequently, DON1.2, DON2 and DONSA1 vectors were constructed through inserting the exon 1, intron A, and/or exon 2 of HCMV ie1 (UL123) gene into the pCM vector (see FIG. 3a, FIG. 3b, and FIGS. 4a to 4c). Then, the DON1.2-CAT, DON2-CAT, and DONSA1-CAT vectors were prepared through the insertion of CAT reporter gene. Cell lines transfected or transduced with these vectors were brought to CAT assay. From the result of CAT assay, it was confirmed that all three vectors showed much higher efficiencies of splicing and gene expression than the control vector L-CAT-SN (see Table 2).

Figure 5:
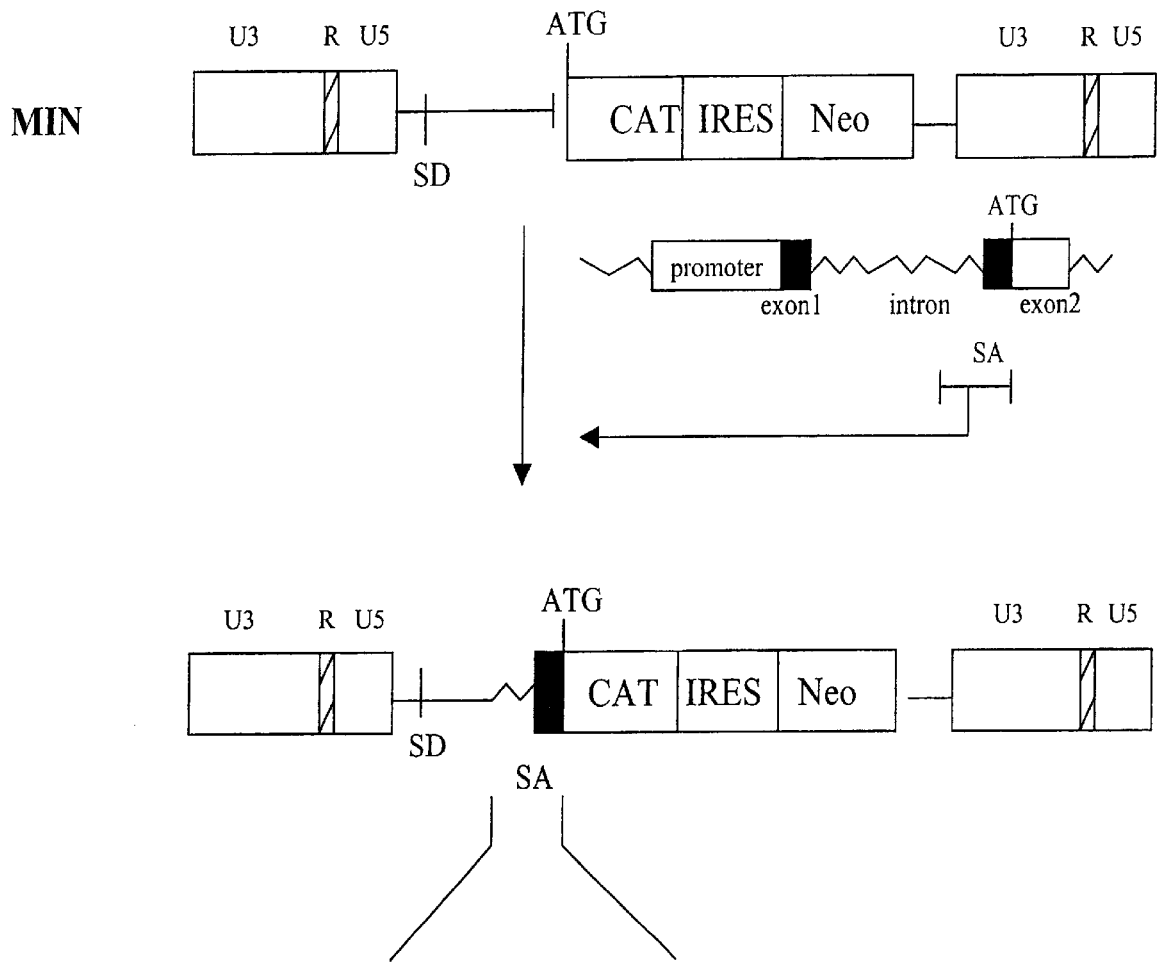

3. The Insertion of Cellular DNA Sequences which Can Promote Splicing and Gene Expression: MIN-AI, MIN-EI, and MIN-GI Construction In another preferred embodiment, retroviral vectors were further devised so that the balance of splicing rate and gene expression rate might lead to higher efficiencies both of viral titers and of gene expression. In these vectors, the exon and/or intron sequences of human genes were inserted into the upstream position of cloning site for foreign gene in the retroviral vectors (see FIG. 5).

To construct these vectors, MIN vector was prepared where all of retroviral coding region was deleted; MLV-derived 5' and 3' LTR were maintained; and EMCV IRES-neo cassette was employed as a heterologous internal promoter. Especially, MIN vector was prepared through following steps: the amplification of a DNA fragment containing MLV 5' and 3' LTR region, the insertion of this fragment into pUC18 vector, and the insertion of IRES-neo cassette into the recombinant vector (see FIG. 6). A DNA fragment containing the partial intron and partial exon 2 of human β-actin, EF1α, or GAPDH gene, was inserted into the upstream position of the cloning site of MIN vector, constructing MIN-AI, MIN-EI, or MIN-GI vector, respectively (see FIGS. 7a to 7c).

To compare the vector using cellular gene as a splicing acceptor (e.g. MIN-AI, etc.) with one using a viral gene (e.g. DON1.2, etc.), another MLV-based vector MIN-2 was prepared. Specifically, DNA sequence containing the partial intron A and partial exon 2 of HCMV ie1 (UL123) gene is inserted into MIN vector (see FIG. 7d). This insert is identical to that of DON2 vector.

Then, MIN-CAT, MIN-AICAT, MIN-EICAT, MIN-GICAT and MIN-2CAT vectors were prepared through the insertion of CAT reporter gene into the corresponding vector. Cell lines transfected or transduced with these vectors were brought to CAT assay. The result of the CAT assay disclosed that the viral titers of all the vectors of this invention are similar to, those of control vectors LXSN and MFG, while the gene expression levels in cell lines transfected or transduced with MIN-2 and MIN-EI are much higher than cell lines containing the control vectors (see Table 3).

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1
The Deletion of Pol Gene from MON Vector
(1-1) ΔSA Construction

To prepare the 5' LTR downstream sequence lacking pol coding sequence, PCR (; Polymerase Chain Reaction) was performed, wherein MON vector (KOREA PATENT APPLICATION NO: 97-48095) was employed as a template and two single-stranded synthetic oligonucleotides described by SEQ ID NO: 1 (HHIR primer) and NO: 2 (R523Bam primer) were as primers. The amplified DNA fragments corresponded to the nucleotide sequence from MLV 5' LTR to +523 bp (see FIG. 1). In this case, +1 represents the transcription start site of MLV genome, and the sequence from +212 to +523 bp is a non-coding sequence that is required to package genomic RNA.

The PCR product was subcloned into pCRII (Invitrogen, CA, USA), and then the HindIII-BamHI fragment was prepared from the resulting vector. A partial HindIII-BamHI fragment of MON vector was replaced with the HindIII-BamHI fragment of PCR product, constructing ΔSA vector. This ΔSA vector is used as an elementary backbone of retroviral vectors which contain MLV 5' and 3' LTR, and 5' non-coding sequence comprising a splicing acceptor, IRES-neo cassette and polypurine track, with all of retroviral coding sequences deleted (see FIG. 1).

(1-2) ΔSA-CAT Construction

To investigate the effect of the above genetic manipulation on the foreign gene expression and on the packaging of retroviral genomic RNA, a bacterial CAT gene was employed as a reporter gene.

CAT gene was obtained through PCR, in which pCAT3-basic vector (Promega, WI, USA) was used as a template land two synthetic oligonucleotides described by SEQ ID NO: 3 (CATATGN primer) and NO: 4 (CATSTOP primer) were as primers. The PCR product was inserted into the pCRII (Invitrogen, CA, USA), and the BamHI fragment of the resulting vector, containing CAT gene, was introduced into pC3.1 (Invitrogen, CA, USA) to prepare pC3.1-CAT. ΔSA-CAT vector was constructed through the insertion of CAT gene (Klenow-treated XbaI-HindIII fragment of pC3.1-CAT) into the HpaI site of ΔSA vector (see FIG. 1).

(1-3) CAT Assay

ΔSA-CAT and control vector (MON-CAT), together with Gag-Pol and Env packaging vectors, were transfected to 293T cells (DuBridge et al., Mol. Cell. Biol., 7: 379–387, 1987). After the transfected cells were cultured for 48 hours, cytosolic proteins were extracted to measure CAT activity, an indicator of foreign gene expression level. Meanwhile, cell-free viral supernatants, obtained by filtrating the cultured medium with 0.45-um filter, were used to transduce NIH3T3 cells (ATCC CRL 1658). The level of CAT activity was determined using the protein extract 48 hours after the transduction.

CAT assay was performed as follows: first, cells were harvested and washed with 1 ml of PBS (phosphate-buffered saline), and then resuspended in 0.25 M Tris buffer (pH 7.5). The cells were lyzed through repeating freezing (in dry ice)—thawing (in 37(C. water bath) cycle 6 times. After the resulting cell extract was heated at 60° C. for 7 minutes to inactivate deacetylase, it was centrifuged at 12,000 rpm for 10 minutes and the supernatant was rescued. The protein level in the extract was quantified according to Bradford's method. The normalized extract was mixed with 1 ul of $^{14}$C-chloramphenicol (60 mCi/mmole, 0.1 mCi/ml), 2 ul of acetyl-coenzyme A (40 mM), and appropriate volume of 0.25 M Tris (pH 7.5). This reaction mixture was incubated 37° C. for appropriate reaction time. After the reaction, chloramphenicol was extracted with ethyl acetate and concentrated under reduced pressure. The pellet was resuspended in 15 ul of ethyl acetate and loaded onto thin layer chromatography (TLC) plate. After TLC was performed using TLC developing solvent (95% choloroform, 5% methanol), TLC plate was dried and then exposed to X-ray film or brought to phosphoimage analyzer, so that the acetylation level of chloramphenicol may be measured. CAT activity in a sample could be calculated from the radioactivity ratio of acetylated chloramphenicol to total chloramphenicol.

Table 1 shows that CAT activity in 293T cell line transfected with ΔSA-CAT lacking pol gene was lower than in control line transfected with MON-CAT. This suggests that pol coding sequence be involved in the regulation of gene expression. In addition, CAT activity in transduced line showed the similar pattern to that in transfected line, implying that the packaging efficiency is related to the gene expression efficiency.

TABLE 1

The effect of pol deletion on gene expression level

| | Cell line | |
|---|---|---|
| Vector | 293T cells | NIH3T3 cells |
| MON-CAT | 1.0 | 1.0 |
| ΔSA-CAT | 0.5 ∓ 0.1 | 0.4 ∓ 0.1 |

Example 2

The Insertion of Promoter and Exon and/or Intron of HCMV ie1 (UL123) Gene

In order to keep the balance of splicing rate and translation rate as well as to enhance the overall yield of viral RNA, MON-derived retroviral vectors comprising the following three vectors were constructed:

DON1.2 vector where the full-length U3 sequence of MLV 5' LTR is replaced with HCMV major immediate early promoter; and MLV splicing acceptor is replaced with a DNA fragment containing the exon 1, intron A and partial exon 2 (which ends just before start codon) of HCMV ie1 (UL123) gene, DON2 vector where the full-length U3 sequence of MLV 5' LTR Is replaced with HCMV major immediate early promoter; and MLV splicing acceptor is replaced with DNA fragment containing the partial intron A and partial exon 2 of HCMV ie1 (UL123) gene, and DONSA1 vector where the full-length U3 sequence of MLV 5' LTR is replaced with HCMV major immediate early promoter; and MLV splicing acceptor is replaced with a DNA fragment containing the splicing acceptor of mouse immunoglobulin gene and the exon 1 of HCMV ie1 (UL123) gene The detailed method of constructing these vectors is described as follows (see FIG. 3a, FIG. 3b, and FIGS. 4a to 4c).

(2-1) SN-3LTR Construction

In three variant vectors, SV40 promoter-neo cassette is inserted into the downstream position of cloning site for a foreign gene (see FIG. 2). To construct these variant vectors, a vector containing SV40 promoter-neo cassette was prepared as follows (see FIGS. 3a and 3b).

To prepare a vector where neo gene is expressed under the control of SV40 promoter, SV40 promoter-neo cassette was produced through PCR. In the PCR, pC3.1 (Invitrogen, CA, USA) was employed as a template, and two synthetic oligonucleotides described by SEQ ID NO: 5 (SV40-5 primer) and NO: 6; (Neo-3 primer) were as PCR primers.

After the SV40 promoter-neo cassette was subcloned in pCRII (Invitrogen, CA, USA), the BamHI-XhoI fragment of the resulting vector was inserted into the BamHI/XhoI site of MON. The resulting vector, MSN was digested with BamHI and EcoRI restriction enzymes, and the BanHI-EcoRI fragment containing SV40 promoter-neo cassette and 3' LTR was ligated with the BamHI-EcoRI fragment of pUC18 so as to construct SN-3LTR vector (see FIG. 3a).

(2-2) pCM Construction

PCR was performed in order to prepare retroviral vector where 5' LTR was replaced with a strong heterologous promoter. Employed as a PCR template was a retroviral vector MCC-CAT (KOREA PATENT APPLICATION NO: 97-48095) containing chimeric LTR in which full-length U3 sequence (−419 to −1 bp) of MLV 5' LTR was replaced with the full-length HCMV major immediate early promoter.

PCR primers were two synthetic oligonucleotides, described by SEQ ID NO. 1 (HHIR primer) and NO: 2 (R523Bam primer). The PCR products contained the DNA sequence from chimeric 5' LTR to +523 bp and subcloned in pCRII (Invitrogen, CA, USA). The HindIII-BamHI fragment of the subcloned sequence was inserted into the HindIII-BamHI site of SN-3LTR vector (obtained in Example 2-1) to prepare pCM vector (see FIG. 3b). In the pCM, all of the retroviral coding sequences were deleted just like ΔSA vector of Example 1-1, while 5' LTR and IRES-neo cassette of ΔSA vector were replaced with chimeric LTR and SV40 promoter-neo cassette, respectively. The pCM vector was employed as a starting material for DON1.2, DON2 and DONSA1 vector, as shown in Example 2-3 to 2-5.

(2-3) DON1.2 and DON1.2-CAT Construction

To obtain DNA fragment containing the exon 1, intron A and exon 2 (to start codon) of HCMV ie1 (UL123) gene, PCR was performed. Template in the PCR was pEQ276 vector (Biegalke et al., Virology, 183: 381–385, 1991) containing DNA sequence from HCMV major immediate early promoter to the exon 5. Two PCR primers were described by SEQ ID NO: 7 (RI5 primer, hybridized with the exon 1) and NO: 8 (CMVexon2.3 primer, hybridized with the exon 2), respectively. 1-kb DNA fragment was amplified in the PCR and contained the exon 1, intron A, and partial exon 2 (which ends just before start codon) of HCMV ie1 (UL123) gene.

The PCR product was inserted into pZero-blunt vector (Invitrogen, CA, USA) to prepare pZero1.2 vector. Then, EcoRI fragment of pZero1.2 was treated with Klenow enzyme to make blunt ends. The pCM vector obtained in Example 2-2 was digested with BamHI enzyme and treated with Klenow enzyme. Two DNA fragments with blunt ends were ligated to construct DON1.2 vector. Additionally, DON1.2-CAT vector was constructed through the insertion of a CAT gene into the Klenow-treated HindIII fragment of DON1.2 (see FIG. 4a).

(2-4) DON2 and DON2-CAT Construction

The HpaI-EcoRI fragment of pZero1.2 of Example 2-3 was prepared, which contained 112-bp 3' region of the intron A and 5' region of exon 2 (from +837 to +964, just before start codon). Then, this DNA fragment was treated with Klenow enzyme to make blunt ends. On the other hand, the pCM vector obtained in Example 2-2 was digested with BamHI enzyme and treated with Klenow enzyme. The above two DNA fragments with blunt ends were ligated to construct DON2 vector. Additionally, DON2-CAT vector was constructed through the insertion of a CAT gene into the Klenow-treated HindIII fragment of DON2 (see FIG. 4b).

(2-5) DONSA1 and DONSA1-CAT Construction

To prepare the splicing acceptor of mouse immunoglobulin gene, single-stranded oligonucleotides were synthesized, which were described by SEQ ID NO: 9 (SA Top oligomer) and NO: 10 (SA bottom oligomer), respectively. Annealing reaction of the two oligomers produced splicing acceptor fragments with cohesive ends. pGEM4-SA vector was prepared through the insertion of the fragment into the BamHI site of pGEM4 vector (Promega, WI, USA) (see FIG. 4c).

To amplify the exon 1 of HCMV ie1 (UL123) gene, PCR was performed, wherein the pEQ276 vector of Example 2-3 was employed as a template and two synthetic oligonucleotides described by SEQ ID NO: 7 (RI5 primer) and NO: 11 (exon 13 primer), respectively, as primers.

The amplified exon 1 fragment was subcloned in the EcoRI site of pZero-blunt vector (Invitrogen, CA, USA), producing pZero-exon1 vector. Then, EcoRI fragment of pZero-exon1 was subcloned in the EcoRI site of the pGEM4-SA to prepare pGEM-SA-exon1 vector.

The XbaI-BamHI fragment of pGEM4-SA-exon1 was treated with Klenow to make blunt ends, and then ligated with the Klenow-treated BamHI fragment of pCM (obtained in Example 2-2), constructing DONSA1 vector.

Figure 4A:
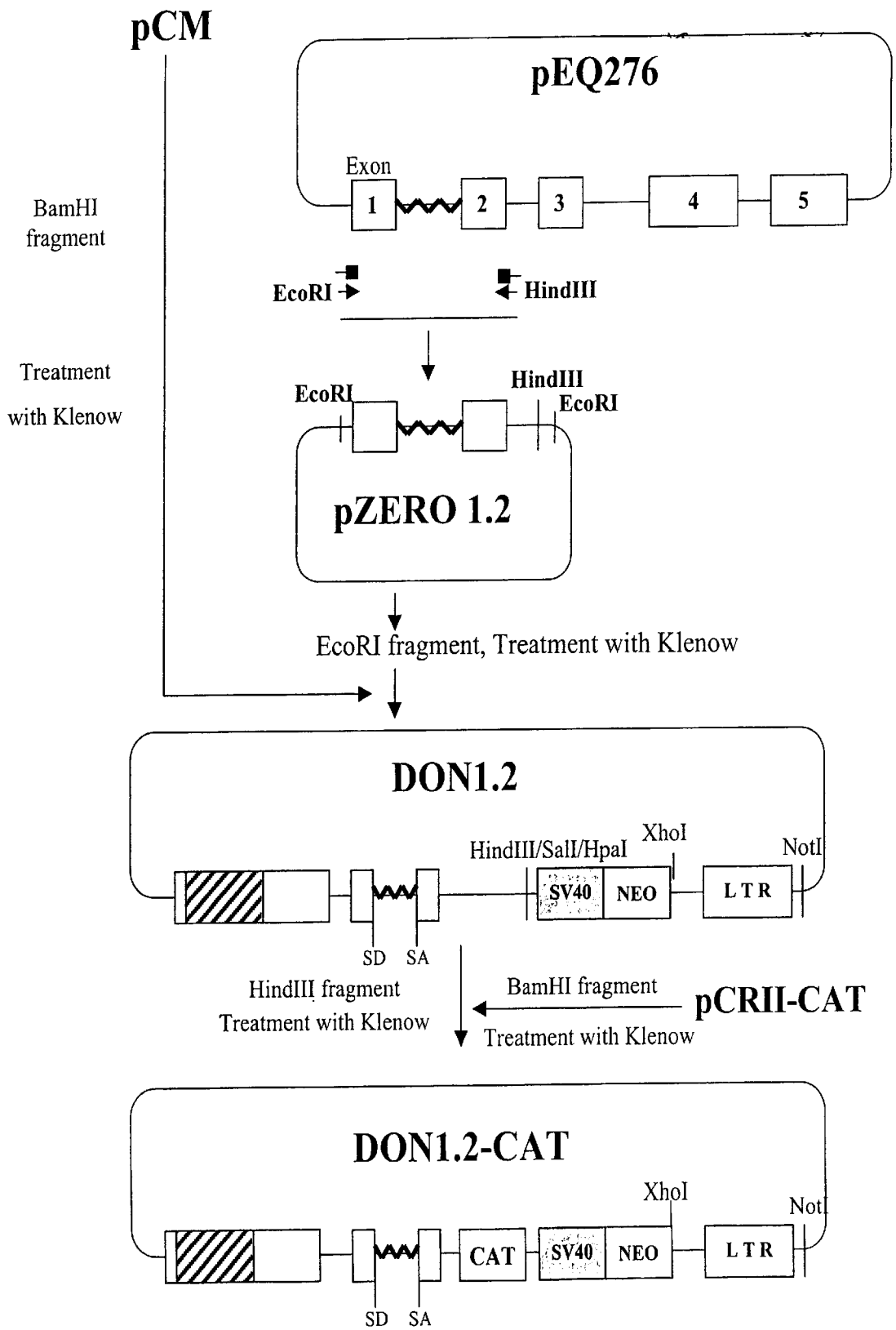
Figure 4B:
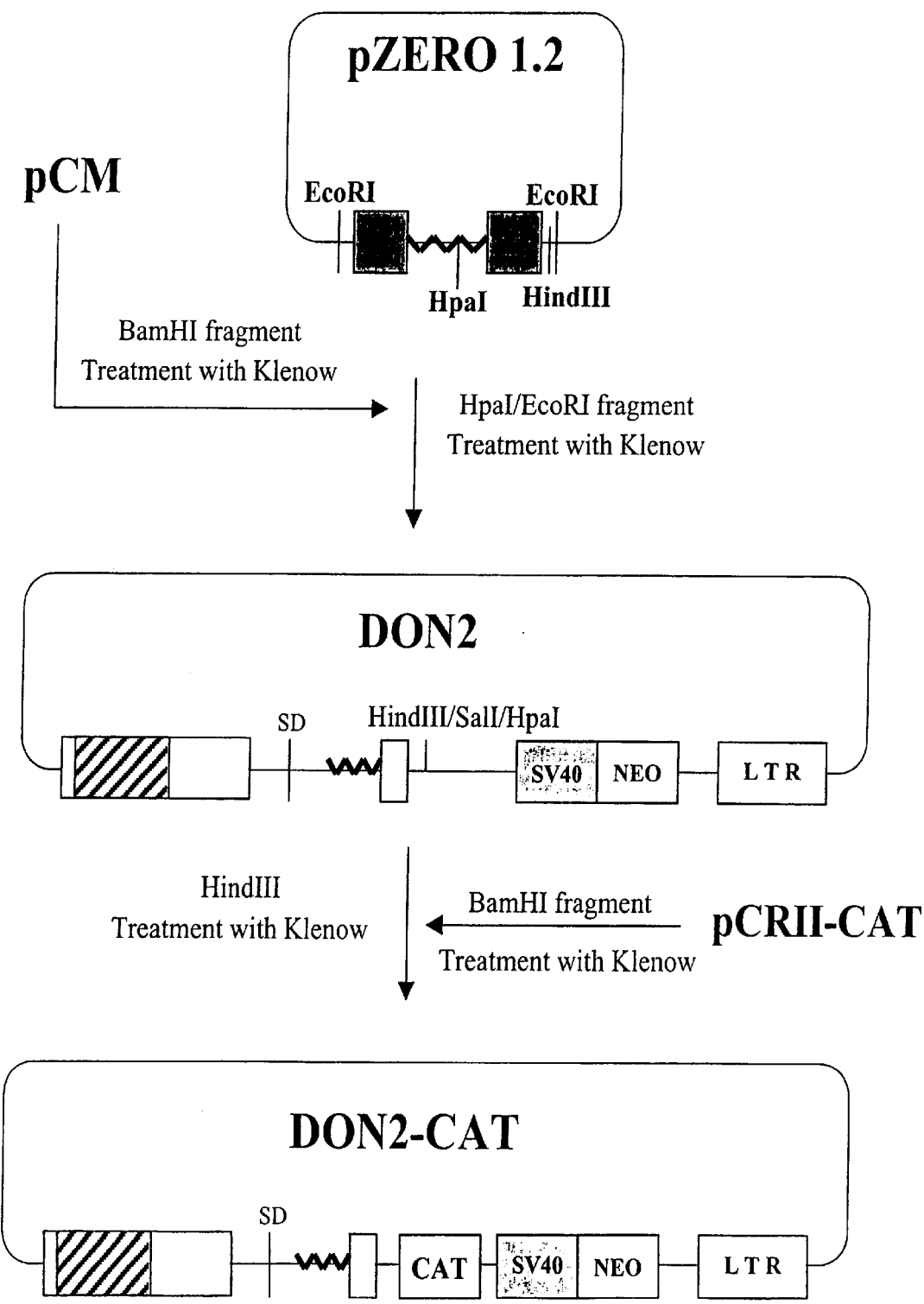
Figure 4C:
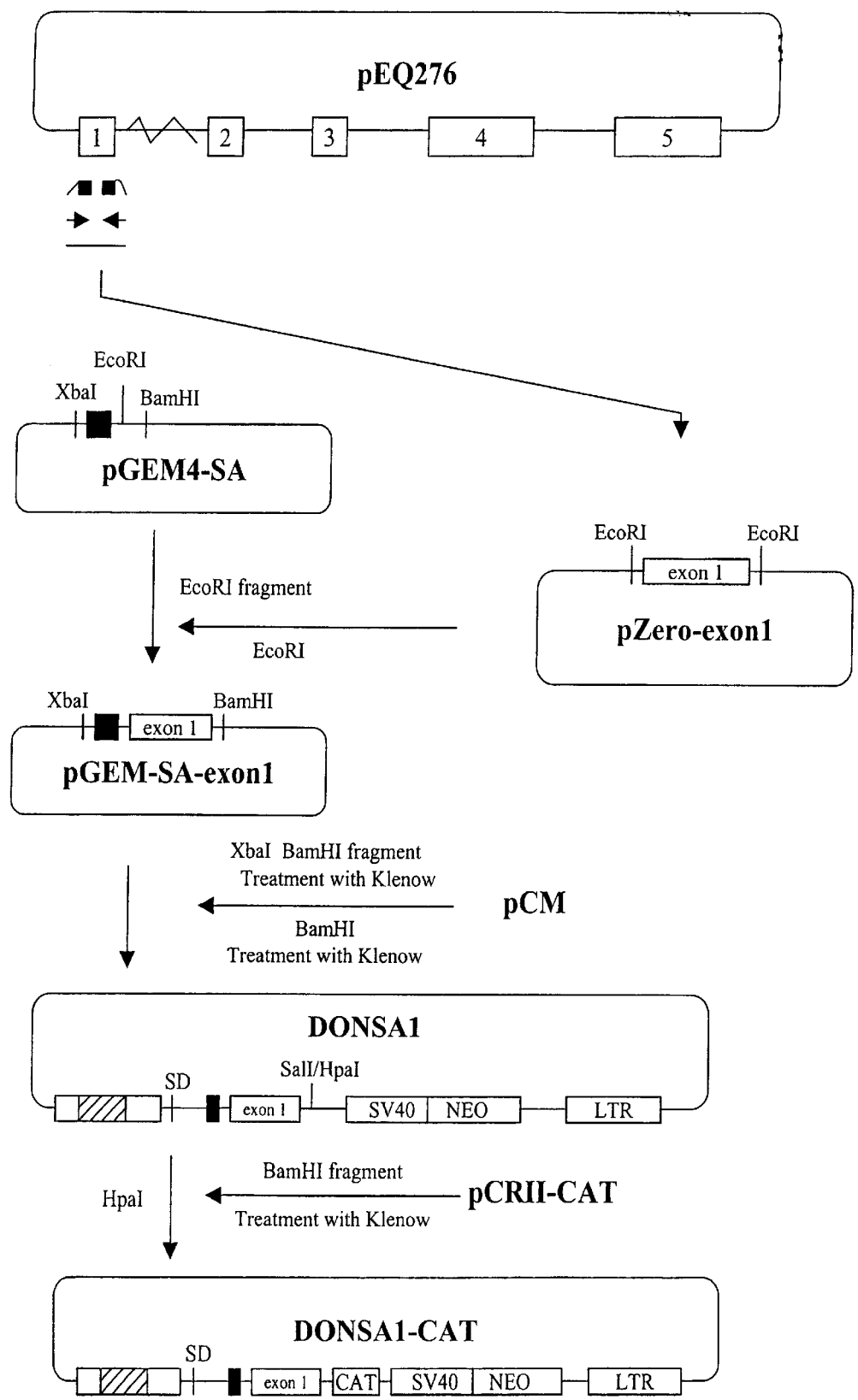

Additionally, DONSA1-CAT vector was constructed through the insertion of CAT gene into the HpaI site of DONSA1 (see FIG. 4c).

(2-6) CAT Assay

DON1.2-CAT, DON2-CAT, DONSA1-CAT and L-CAT-SN vector were transfected to packaging line FlyA13 (Cosset et al., J. Virol., 69: 7430–7436, 1995). After the transfected lines were cultured for 48 hours, cell-free viral supernatants were prepared to transduce NIH3T3 cells. The transduced lines were cultured for 48 hours. CAT activities in the transfected or transduced lines were measured according to the method of Example 1-3, thereby analyzing the relative gene expression levels.

As shown in Table 2, markedly higher level of CAT activity was observed in FlyA13 line transfected with DON1.2-CAT or DON2-CAT than in a control line (transfected with L-CAT-SN). In addition, NIH3T3 cells transduced stably with DON1.2-CAT or DON2-CAT vector showed 5- to 10-fold higher CAT activity than control cells did. In case of cell line transfected or transduced with DONSA1-CAT, a little higher CAT activity was observed than in control. These results suggested that splicing efficiency and gene expression efficiency can be elevated if a heterologous non-coding sequence involved in splicing is inserted into the upstream position of foreign gene in an expression vector.

E. coli strains transformed with DON2 and DONSA1 vector were designated TOP10-DON2 and Top10-DONSA1, respectively. They were deposited in Korean Culture Center of Microorganism, (KCCM at 361-221, Yurim B/D, Hongje-Dong, Seodaemun-Ku, Seoul 120-091, Korea) under the terms of the Budapest Treaty on Jun. 5, 1998 (accession NO: KCCM-10128, KCCM-10127, respectively).

TABLE 2

The effect of the heterologous sequence insertion on the gene expression level

| | Cell line | |
| --- | --- | --- |
| Vector | FlyA13 | NIH3T3 |
| L-CAT-SN | 1.0 | 1.0 |
| DON1.2-CAT | 10.1 ∓ 1.5 | 7.7 ∓ 1.6 |
| DON2-CAT | 12.5 ∓ 2.1 | 8.0 ∓ 2.0 |
| DONSA1-CAT | 5.0 ∓ 2.0 | 1.8 ∓ 1.2 |

Example 3

The Insertion of the Intron and/or Exon of Human Gene

In this Example, MIN-derived retroviral vectors, MIN-AI, MITN-EI, MIN-GI and MIN-2 were constructed, so that the rates of transcription, splicing and translation of a foreign gene might be balanced in eukaryotic cells. None of viral sequences are contained in MIN vector as well as in ΔSA vector, but MIN contains IRES-neo cassette instead of SV promoter-neo cassette (see FIG. 5). The features of the above four vectors are as follows:

A DNA fragment containing the intron, splicing acceptor and partial exon 2 of human β-actin gene was inserted into the upstream position of foreign gene in MIN-AI vector.

A DNA fragment containing the intron, splicing acceptor and partial exon 2 of human EF1α gene was inserted into the upstream position of foreign gene in MIN-EI vector.

A DNA fragment containing the intron, splicing acceptor and partial exon 2 of human GAPDH gene was inserted into the upstream position of foreign gene in MIN-GI vector.

Besides these constructs, a vector was prepared, where a heterologous, viral sequence was inserted. Especially, MIN-2 vector was prepared where a DNA fragment containing the intron, splicing acceptor and partial exon 2 of HCMV ie1 (UL123) gene was inserted into the upstream position of cloning site of the MIN vector.

MIN and MIN-derived MIN-AI, MIN-EI, MIN-GI and MIN-2 vectors were constructed as follows.

(3-1) MIN Construction

To obtain MLV 3' LTR region, PCR was performed, in which pMLV (Shinnick et al., Nature, 293: 543–548, 1981) was employed as a template and two synthetic oligonucleotide described by SEQ ID NO: 12 (3LTR5 primer) and NO: 113 (3LTR3 primer) were as primers. Amplified PCR product contained the 3' untranslated region, the polypurine track, and the 3' LTR of MLV genome. PCR product subcloned in pCRII vector (Invitrogen, CA, USA) was digested with BamHI and EcoRI enzymes, and the resulting fragment was inserted into the BamHI-EcoRI site of pUC18 to prepare p3LTR vector (see FIG. 6).

On the other hand, to obtain non-coding sequence containing retroviral 5' LTR and splicing donor, PCR was performed, where pMLV was employed as a template and two synthetic oligonucleotides described by SEQ ID NO: 1 (HHIR primer) and NO: 14 (5LTR3 primer) were as primers. Amplified PCR product contained nucleotide sequence from 5' LTR to +623 bp (just before gag coding sequence) of MLV genome. After PCR product was subcloned in pCRII vector, the HindII-BamHI fragment of the vector was inserted into the HindIII-BamHI site of p3LTR to prepare p53LTR vector (see FIG. 6).

Figure 6:
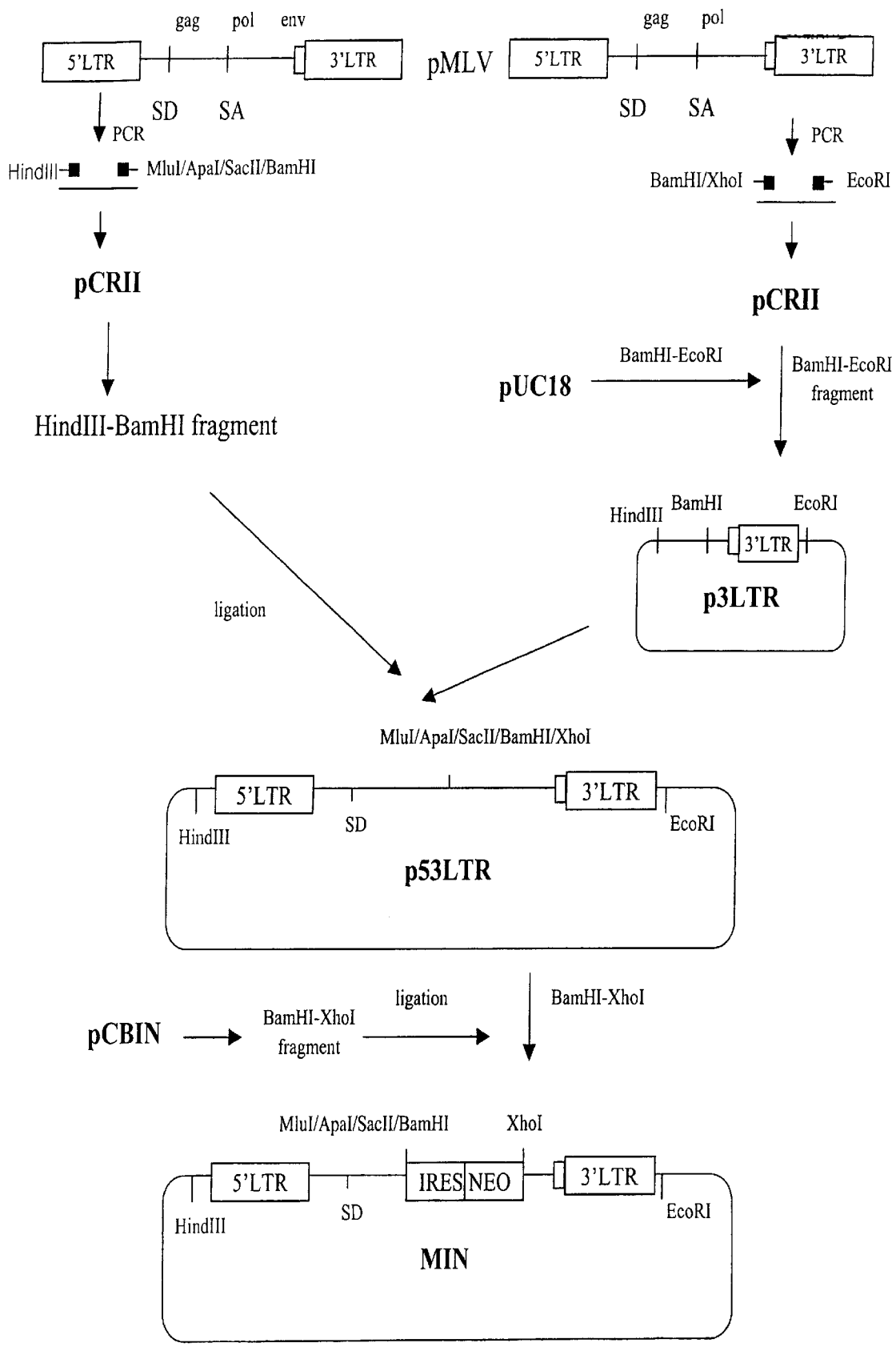

Finally, IRES/neo cassette were isolated from pCBIN (KOREA PATENT APPLICATION NO: 97-48095) through BamHI-XhoI digestion, and then inserted into BamHI-XhoI site of the p53LTR vector to construct MIN vector (see FIG. 6).

MIN-CAT vector was also constructed through the insertion of a CAT gene into the BamHI site of MIN vector so as to analyze the expression efficiency of MIN vector.

(3-2) MIN-AI Construction

To prepare human nucleotide sequences that would be inserted into MIN vector, genomic DNA was extracted from human cells. First, peripheral blood mononuclear cells were separated from human blood by Ficoll-paque gradient centrifugation. After washed once or twice and gathered again, the cells were lysed with TES (10 mM Tris-Cl (pH 7.0), 10 mM EDTA, 0.7% SDS). Proteinase K (400 Ug/ml) was added to the cell lysate, and the lysate was incubated at 50–55(C. for 1–2 hours, followed by phenol/chloroform extraction and ethanol precipitation.

The isolated genomic DNA was employed as a template in PCR, which amplified DNA fragment containing the promoter, exon 1, intron and partial exon 2 of human β-actin gene. The PCR primers were two synthetic oligonucleotides described by SEQ ID NO: 15 (beta-actin 5 primer) and NO: 16 (beta-actin 3 primer). The PCR product was subcloned in pCRII vector, and then the MluI-NheI fragment of the vector was inserted into the MluI-NheI site of pC3.1 vector (Invitrogen, CA, USA) to prepare pβactin.

Figure 7A:
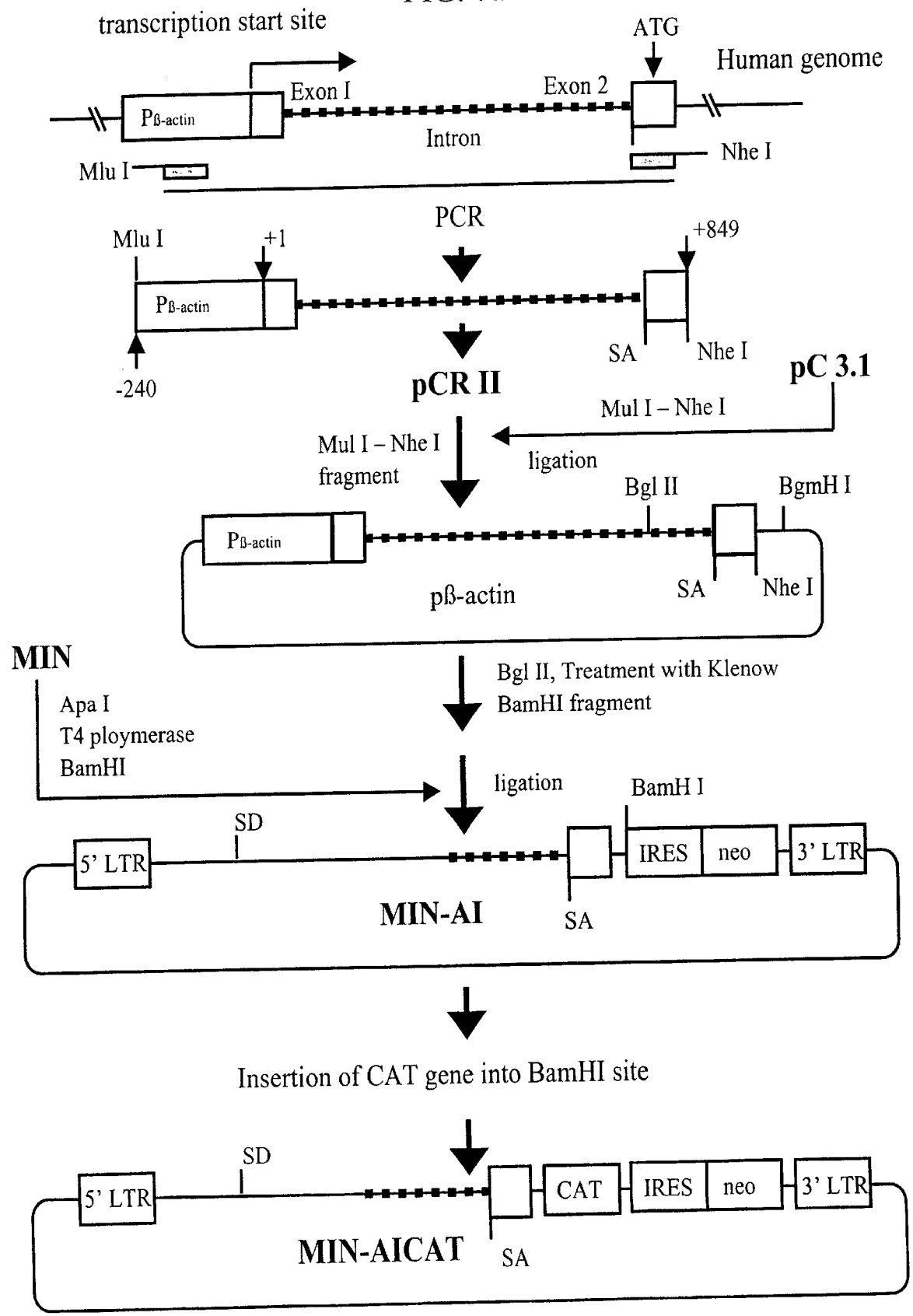
FIG. 7a represents the procedure of MIN-AI construction, wherein a genomic PCR product containing human (β-actin gene is obtained, and then a DNA fragment containing the partial intron 1, splicing acceptor and partial exon 2 of human (β-actin gene is inserted into the MIN vector.

The Klenow-treated BglI-BamHI fragment of pβactin (corresponding to +717~+849 of human β-actin gene) was inserted into the T4-polymerase-treated ApaI/BamHI site of MIN vector (see FIG. 7a). The resulting vector was designated MIN-AI.

In addition, MIN-AICAT vector was constructed through the insertion of a CAT gene into the BamHI site of MIN-AI vector so as to analyze the expression efficiency of MIN-AI.

(3-3) MIN-EI Construction

To obtain the non-coding sequence of human EF1(gene, genomic PCR was performed. The genomic DNA isolated in Example 3-2 was employed as a template in the PCR, and two synthetic oligonucleotides described by SEQ ID NO: 17 (EF1α5 primer) and NO: 18 (EF1α3 primer) were as PCR primers. The PCR product contained the promoter, exon 1, intron and partial exon 2 of human EF1α gene. The PCR product was subcloned in pCRII vector, and then the MluI-NheI fragment of the vector was inserted into the MluI-NheI site of pC3.1 vector (Invitrogen, CA, USA) to prepare pEF1α.

Figure 7B:
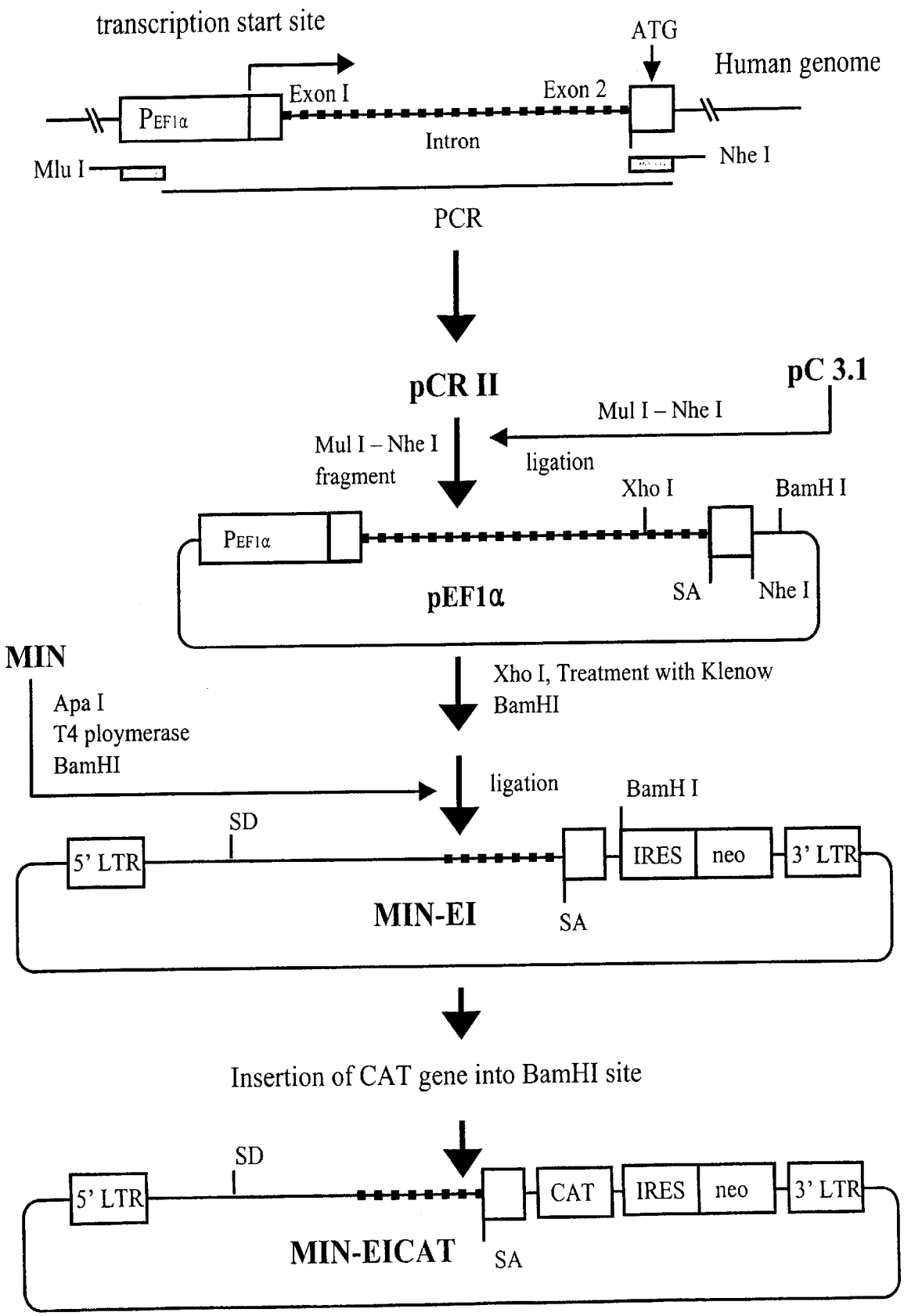
FIG. 7b represents the procedure of MIN-EI construction, wherein a genomic PCR product containing human EF1α gene is obtained, and then a DNA fragment containing the partial intron 1, splicing acceptor and partial exon 2 of human EF1α gene is inserted into the MIN vector.
Figure 7C:
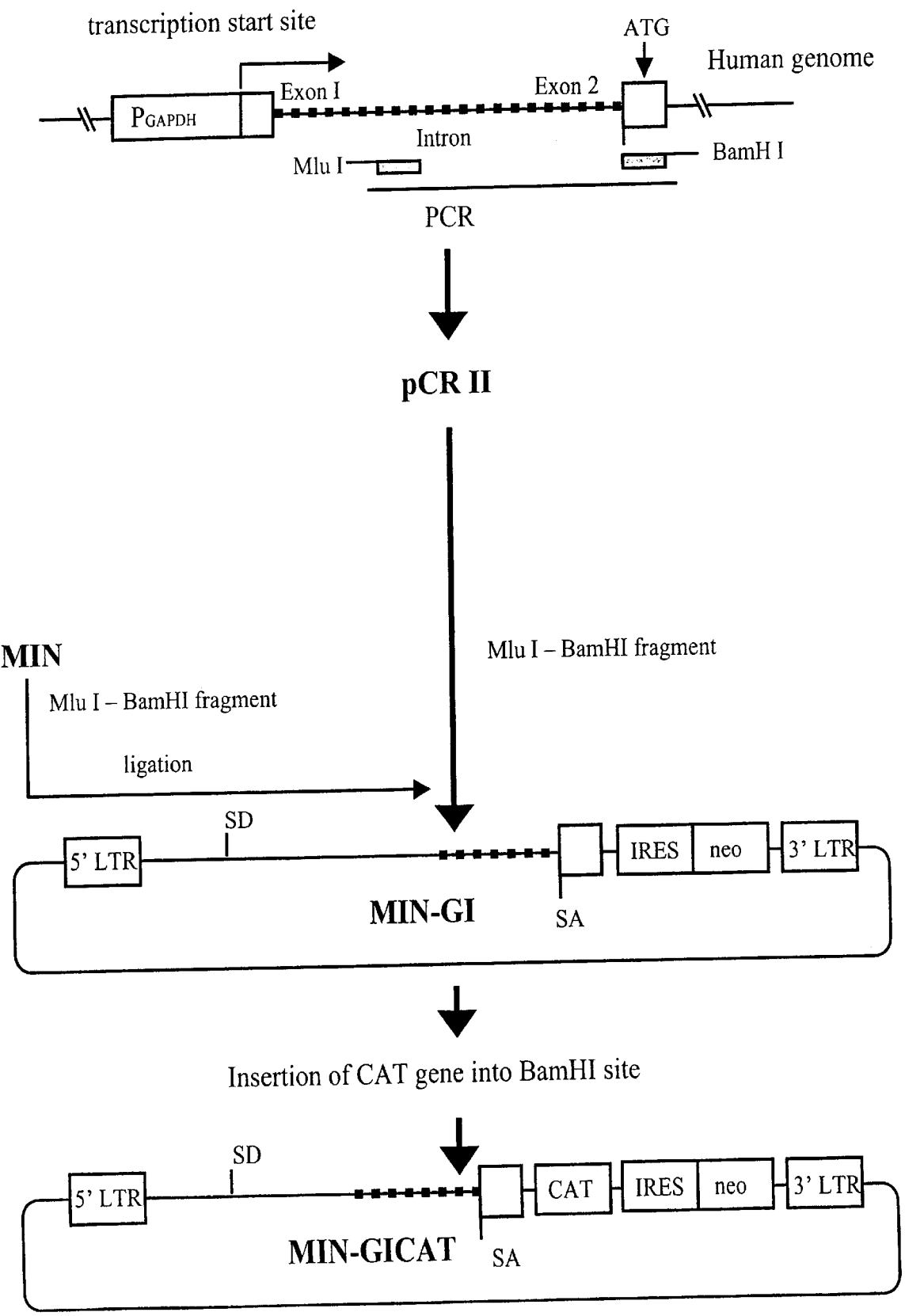
FIG. 7c represents the procedure of MIN-GI construction, wherein a DNA fragment containing the partial intron 1, splicing acceptor and partial exon 2 of human GAPDH gene is obtained through genomic PCR and then inserted into the MIN vector.
Figure 7D:
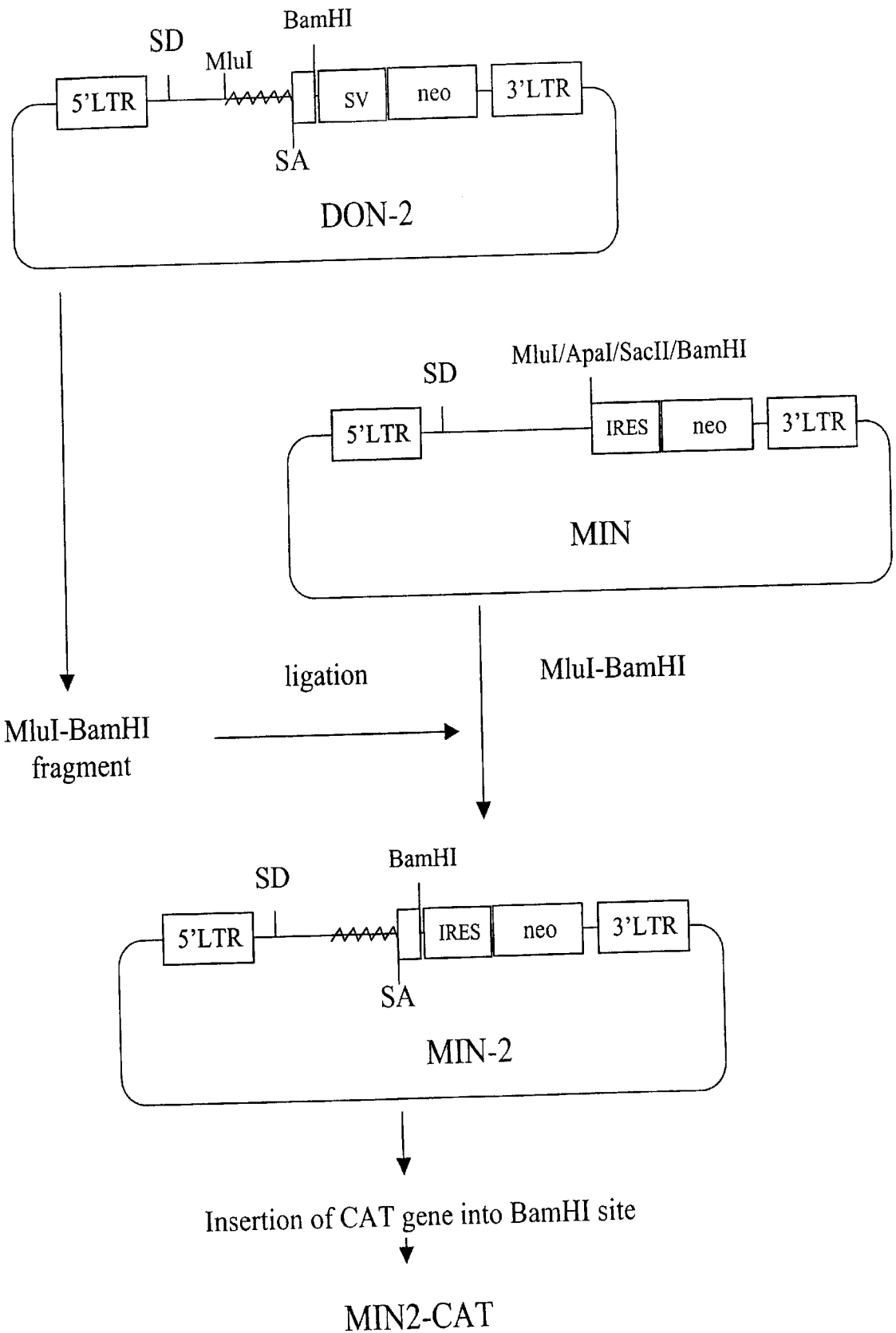
FIG. 7d represents the procedure of MIN-2 construction, wherein a DNA fragment containing the partial intron A, splicing acceptor and partial exon 2 of HCMV ie1 (UL123) gene is inserted into the MIN vector.

The Klenow-treated XhoI-BamHI fragment of pEF1α (corresponding to +772~+1008 of human EF1α gene) was inserted into the T4-polymerase-treated ApaI-BamHI site of MIN vector (see FIG. 7b). The resulting vector was designated MIN-EI.

In addition, MIN-EICAT vector was constructed through the insertion of CAT cassette into the BamHI site of MIN-EI vector in order to analyze the expression efficiency of MIN-EI vector. The MIN-EICAT was introduced into *E. coli* strain Top10, and the *E. coli* transformant was designated MIN-EICAT (Top10) and deposited in Korean Culture Center of Microorganisms, (KCCM at 361-221, Yurim B/D, Hongje-Dong, Seodaemun-Ku, Seoul 120-091, Korea) under the terms of the Budapest Treaty on Jun. 2, 1999 (Accession NO: KCCM-10163).

(3-4) MIN-GI Construction

To obtain the non-coding sequence of human GAPDH gene, genomic PCR was performed. The genomic DNA isolated in Example 3-2 was employed as a template in the PCR, and two synthetic oligonucleotides described by SEQ ID NO: 19 (Gint5 primer) and NO: 20 (Gint3 primer) were as PCR primers. The PCR product contained the partial intron and partial exon 2 of human GAPDH gene, corresponding to +185~+317 of human GAPDH gene. The PCR product was subcloned in pCRII vector, and then the MluI-BamHI fragment of the vector was inserted into the MluI-BamHI site of MIN vector. The resulting vector was designated MIN-GI (see FIG. 7c).

In addition, MIN-GICAT vector was constructed through the insertion of a CAT gene into the BamHI site of MIN-GI vector in order to analyze the expression efficiency of MIN-GI vector.

(3-5) MIN-2 Construction

The MluI-BamHI fragment of DON2 (corresponding to +837~+964 of HCMV ie1 gene) was prepared, which contained the intron, splicing acceptor and partial exon 2 of HCMV ie1 (UL123) gene. This MluI-BamHI fragment was inserted into the MluI-BamHI site of MIN vector (see FIG. 7d). The resulting vector was designated MIN-2.

In addition, MIN-2CAT vector was constructed through the insertion of CAT gene into the BamHI site of MIN-2 so as to analyze the expression efficiency of MIN-2 vector. The MIN-2CAT was introduced into *E. coli* strain Top10. The *E. coli* transformant was designated MIN-2CAT(Top10) and deposited in Korean Culture Center of Microorganisms, (KCCM at 361-221, Yurim B/D, Hongje-Dong, Saeodaemun-Ku, Seoul 120-091, Korea) under the terms of the Budapest Treaty on Jun. 2, 1999 (Accession NO: KCCM-10164).

(3-6) CAT Assay

To investigate the foreign gene expression efficiencies and the packaging capabilities of the above four vectors, the 5 vectors were brought to CAT assay, wherein the CAT-inserted forms of well-known retroviral vectors, MFG and LXSN, were employed as control vectors (Miller et al., Biotechniques, 7: 980–990, 1989; Ohashi et al., Proc. Natl. Acal. Sci. USA, 89: 11332–11336, 1992). The packaging line Phoenix (Kinsella and Nolan, Hum. Gene. Ther. 7: 1405–1413) was transfected with these vectors and then cultured for 48 hours. Meanwhile, cell-free viral supernatants, obtained by filtrating the cultured medium with 0.45 um filter, were used to transduce NIH3T3 cells (ATCC CRL 1658). The level of CAT activity was determined using the protein extract 2 days after transduction. CAT activity was measured in cell line transfected or transduced with each vector (see the columns "transiently transfected" and "transduced, transient" in Table 3) as well as in antibiotics-resistant cell population (see the column "transduced, stable" in Table 3). Additionally, CAT activity was measured in the stable cell population subcultured for 4 weeks (see the column "transduced, stable (4 weeks)" in Table 3). The gene expression levels and the viral titers in transfected lines were determined from CAT activities that were measured in transfected or transduced line with each vector.

As shown in Table 3, all the retroviral vectors showed higher CAT activities than MIN vector, except for LXSN vector. However, the CAT activities were varied, depending on the heterologous sequence inserted. Especially, MIN-EI and MIN-2 produced strikingly high levels of gene expression. It was quite remarkable that the cells transduced stably with MIN-EI or MIN-2 produced far higher gene expression levels, even after the subculture for 4 weeks.

TABLE 3

The effect of heterologous sequences on the efficiency of retroviral vectors

| | Relative CAT activity | | | Relative viral titer |
|---|---|---|---|---|
| Vector | Tran-siently transfected | Transduced Transient | Stable | Stable (4 weeks) | |

| Vector | Transiently transfected | Transient | Stable | Stable (4 weeks) | Relative viral titer |
|---|---|---|---|---|---|
| MIN-CAT | 1.0 | 1.0 | 1.0 | 1.0 | 1.0 |
| MIN-2CAT | 3.5 ∓ 0.5 | 3.7 ∓ 0.5 | 4.5 ∓ 0.5 | 2.3 ∓ 0.5 | 0.9 ∓ 0.3 |
| MIN-1ICAT | 0.9 ∓ 0.2 | 1.1 ∓ 0.2 | 1.1 ∓ 0.2 | 0.9 ∓ 0.2 | 0.8 ∓ 0.2 |
| MIN-EICAT | 3.5 ∓ 0.4 | 3.3 ∓ 0.4 | 3.5 ∓ 0.4 | 2.7 ∓ 0.4 | 1.1 ∓ 0.2 |
| MIN-GICAT | 2.0 ∓ 0.5 | 2.4 ∓ 0.3 | 2.2 ∓ 0.4 | 1.5 ∓ 0.3 | 1.3 ∓ 0.2 |

TABLE 3-continued

The effect of heterologous sequences on the efficiency of retroviral vectors

| Vector | Transiently transfected | Transient | Stable | Stable (4 weeks) | Relative viral titer |
|---|---|---|---|---|---|
| MFC-CAT | 1.0 ∓ 0.2 | 1.1 ∓ 0.3 | 0.8 ∓ 0.2 | 0.3 ∓ 0.1 | 1.0 ∓ 0.3 |
| LXSN-CAT | 0.2 ∓ 0.1 | 0.2 ∓ 0.1 | 0.2 ∓ 0.1 | 0.1 ∓ 0.0 | 0.5 ∓ 0.2 |

Industrial Applicability

As disclosed and verified above, this invention provides retroviral vectors which have many advantages for gene therapy and so on. The vectors of this invention have following features:

1. Since all of retroviral coding sequences (gag, env, and pol sequences) are deleted, the possibility can be utterly excluded that replication-competent retrovirus is produced through homologous recombination.
2. Since a heterologous intron, splicing acceptor, and/or non-coding sequence are/is inserted into the upstream position of cloning site for a foreign gene, the foreign gene in the vectors can be expressed both stably and efficiently.
3. Since U3 region in 5' LTR is replaced with a heterologous promoter that intensively induces transcription especially in human cells, the human cell-derived packaging lines transfected with the vectors can produce higher levels of RNA and thus show increased viral titers.
4. An IRES or a heterologous promoter is used simultaneously to express two or more foreign genes in the vectors. In this case, a minimal promoter may be employed as the inserted heterologous promoter, in order to diminish an interference of the heterologous internal promoter and to clone a foreign gene with larger size.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A murine leukemia virus (MLV)-based retroviral vector comprising a MLV 5' LTR (long terminal repeat), a MLV packaging signal, a cloning site for a foreign gene, and A MLV 3' LTR in order, wherein the gag, env and pol coding regions of MLV have been completely deleted.

2. The MLV-based retroviral vector of claim 1, which comprises an intron, a splicing acceptor, or both inserted upstream of the cloning site for the foreign gene, said intron and splicing acceptor being heterologous to MLV.

3. The MLV-based retroviral vector of claim 2, wherein the intron is selected from the group consisting of the introns of a human cytomegalovirus (HCMV) IE1 (U123) gene, an elongation factor 1α (EF1α) gene, a glyceraldehyde 3-phosphate dehydrogenase (GAPDH) gene, a β-actin gene and a mouse immunoglobulin gene.

4. The MLV-based retroviral vector of claim 1, which comprises a non-coding sequence inserted upstream of the cloning site for the foreign gene, said non-coding sequence being heterologous to MLV.

5. The MLV-based retroviral vector of claim 4, wherein the non-coding sequence is selected from the group consisting of the non-coding sequences of a HCMV IE1 (UL123) gene, an EF1 α gene, a GAPDH gene and a β-actin gene.

6. The MLV-based retroviral vector of claim 4, wherein the non-coding sequence comprises the HCMV major immediate early promoter.

7. The MLV-based retroviral vector of claim 1, which comprises a promoter inserted downstream of the cloning site for the foreign gene, said promoter being heterologous to MLV.

8. The MLV-based retroviral vector of claim 7, wherein the promoter is the SV40 minimal promoter.

9. The MLV-based retroviral vector of claim 4, which is the DONSA1 vector having the genetic map depicted in FIG. 4c.

10. The MLV-based retroviral vector of claim 2, which is the DON2 vector having the genetic map depicted in FIG. 4b.

11. The MLV-based retroviral vector of claim 2, which is the MIN-EI vector having the genetic map depicted in FIG. 7b.

12. The MLV-based retroviral vector of claim 2, which is the MIN-2 vector having the genetic map depicted in FIG. 7d.

13. The E. coli strain Top10-DONSA1 (Accession No.: KCCM-10127) transformed with the DONSA1 vector of claim 9.

14. The E. coli strain Top10-DON2 (Accession No.: KCCM-10128) transformed with the DONSA1 vector of claim 10.

15. The E. coli strain MIN-EICAT(Top10) (Accession No.: KCCM-10163) transformed with the MIN-EICAT vector which comprises a bacterial chloramphenicol acetyltransferase (CAT) gene in the cloning site of the vector of claim 11.

16. E. coli strain MIN-2CAT(Top10) (Accession No.: KCCM-10164) transformed with the MIN-2CAT vector which comprises a bacterial chloramphenicol acetyltransferase (CAT) gene in the cloning site of the vector of claim 12.

17. The MLV-based retroviral vector of claim 2, wherein the splicing acceptor is selected from the group consisting of the splicing acceptors of a human cytomegalovirus (HCMV) IE1 (UL123) gene, an elongation factor 1α (EF1α) gene, a glyceraldehyde 3-phosphate dehydrogenase (GAPDH) gene, a β-actin gene and a mouse immunoglobulin gene.

18. The MLV-based retroviral vector of claim 1, wherein the full-length U3 sequence (−419 to −1 bp) of MLV 5' LTR is replaced with a promoter heterologous to MLV.

19. The MLV-based retroviral vector of claim 18, wherein the promoter is the HCMV major immediate early promoter.

* * * * *

UNITED STATES PATENT AND TRADEMARK OFFICE
CERTIFICATE OF CORRECTION

PATENT NO.     : 6,451,595 B1
DATED          : September 17, 2002
INVENTOR(S)    : Sunyoung Kim et al.

It is certified that error appears in the above-identified patent and that said Letters Patent is hereby corrected as shown below:

Column 21,
Line 4, "A" should be corrected to -- a --.
Line 13, "(U123)" should be corrected to -- (UL123) --.

Column 22,
Line 20, the word -- The -- should be inserted before "E. Coli".

Signed and Sealed this

Thirteenth Day of May, 2003

JAMES E. ROGAN
*Director of the United States Patent and Trademark Office*